US011553925B2

(12) United States Patent
Hopkinson et al.

(10) Patent No.: US 11,553,925 B2
(45) Date of Patent: Jan. 17, 2023

(54) INFLATABLE COMPRESSION DEVICE

(71) Applicant: Merit Medical Systems, Inc., South Jordan, UT (US)

(72) Inventors: Aaron Hopkinson, Herriman, UT (US); Tyler Rees, Draper, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 16/380,505

(22) Filed: Apr. 10, 2019

(65) Prior Publication Data

US 2019/0314035 A1 Oct. 17, 2019

Related U.S. Application Data

(60) Provisional application No. 62/656,242, filed on Apr. 11, 2018.

(51) Int. Cl.
*A61B 17/135* (2006.01)
*A61B 17/132* (2006.01)
*A61B 17/12* (2006.01)

(52) U.S. Cl.
CPC ........ *A61B 17/135* (2013.01); *A61B 17/1325* (2013.01); *A61B 2017/12004* (2013.01)

(58) Field of Classification Search
CPC .............. A61B 17/135; A61B 17/1325; A61B 2017/12004; A61B 2090/0807; A61B 2017/00907; A61B 2090/3937
See application file for complete search history.

(56) References Cited

U.S. PATENT DOCUMENTS

| 1,281,653 | A | 10/1918 | Plummer |
| 2,332,107 | A | 10/1943 | Nieburgs |
| 3,050,064 | A | 8/1962 | Moore et al. |
| 4,390,519 | A | 6/1983 | Sawyer |
| 4,479,495 | A | 10/1984 | Isaacson |
| 4,557,262 | A | 12/1985 | Snow |
| 4,834,802 | A | 5/1989 | Prier |
| 5,139,512 | A | 8/1992 | Dreiling et al. |
| 5,269,803 | A | 12/1993 | Geary et al. |
| 5,304,186 | A | 4/1994 | Semler et al. |
| 5,304,201 | A | 4/1994 | Rice |

(Continued)

FOREIGN PATENT DOCUMENTS

| CN | 201205292 | 3/2009 |
| CN | 201861701 | 6/2011 |

(Continued)

OTHER PUBLICATIONS

International Search Report and Written Opinion dated Jul. 30, 2019 for PCT/US2019/026785.

(Continued)

*Primary Examiner* — Shaun L David
(74) *Attorney, Agent, or Firm* — Dorsey & Whitney LLP

(57) ABSTRACT

An inflatable compression device configured to apply a compressive force to a puncture site of a patient's vessel, such as an artery is disclosed. The hemostasis device may comprise a location indicium disposed on an inside surface of an inflatable bladder portion of the device so as to be disposed in close proximity to the skin of the patient to improve alignment of the compression device with the puncture site.

7 Claims, 10 Drawing Sheets

(56) References Cited

U.S. PATENT DOCUMENTS

| | | |
|---|---|---|
| 5,613,491 A | 3/1997 | Kanner et al. |
| 5,695,520 A | 12/1997 | Bruckner et al. |
| 5,728,120 A | 3/1998 | Shani et al. |
| 5,779,657 A | 7/1998 | Daneshvar |
| 5,997,564 A | 12/1999 | Shehata et al. |
| 6,068,646 A | 5/2000 | Lam |
| 6,231,507 B1 | 5/2001 | Zikorus et al. |
| 6,647,986 B1 | 11/2003 | Korotko et al. |
| 6,833,001 B1 | 12/2004 | Chao |
| 7,758,574 B2 | 7/2010 | Huh et al. |
| 7,780,612 B2 | 8/2010 | Ross |
| 8,147,417 B2 | 4/2012 | Gavriely |
| 8,632,840 B2 | 1/2014 | Avitable |
| 8,845,680 B2 | 9/2014 | Lampropoulos et al. |
| 9,332,994 B2 | 5/2016 | Pancholy et al. |
| D804,663 S | 12/2017 | Jenkins |
| D821,590 S | 6/2018 | Hylton et al. |
| 10,172,625 B2 | 1/2019 | Wada et al. |
| 10,463,833 B2 | 11/2019 | Clarke et al. |
| 10,492,797 B2 | 12/2019 | Okamura |
| D893,034 S | 8/2020 | Kase et al. |
| 2002/0188315 A1 | 12/2002 | Guzman et al. |
| 2003/0055453 A1 | 3/2003 | Akerfeldt |
| 2003/0139766 A1 | 7/2003 | McEwen et al. |
| 2003/0149359 A1 | 8/2003 | Smith |
| 2005/0113866 A1 | 5/2005 | Heinz et al. |
| 2005/0125025 A1 | 6/2005 | Rioux |
| 2006/0058841 A1 | 3/2006 | Mills et al. |
| 2006/0190026 A1 | 8/2006 | Sanders |
| 2007/0239092 A1 | 10/2007 | Ross |
| 2007/0248810 A1 | 10/2007 | McGee et al. |
| 2007/0270720 A1 | 11/2007 | Fry |
| 2009/0209896 A1 | 8/2009 | Selevan |
| 2009/0240182 A1 | 9/2009 | Weber et al. |
| 2009/0281565 A1 | 11/2009 | McNeese |
| 2010/0211000 A1 | 8/2010 | Killion et al. |
| 2010/0217202 A1 | 8/2010 | Clark |
| 2010/0280541 A1 | 11/2010 | Lampropoulos |
| 2012/0221041 A1 | 8/2012 | Hansson et al. |
| 2012/0238934 A1 | 9/2012 | During |
| 2012/0296369 A1 | 11/2012 | Atthoff et al. |
| 2013/0023734 A1 | 1/2013 | Okamura |
| 2013/0079723 A1 | 3/2013 | Andino et al. |
| 2013/0165787 A1 | 6/2013 | Ukawa et al. |
| 2013/0237866 A1 | 9/2013 | Cohen |
| 2013/0245675 A1 | 9/2013 | Kaisha |
| 2013/0289613 A1 | 10/2013 | Kaisha |
| 2014/0012120 A1 | 1/2014 | Cohen et al. |
| 2014/0012313 A1 | 1/2014 | Finkielsztien et al. |
| 2014/0142615 A1 | 5/2014 | Corrigan, Jr. |
| 2014/0236221 A1 | 8/2014 | Zhadkevich |
| 2014/0288408 A1 | 9/2014 | Deutsch |
| 2015/0018868 A1 | 1/2015 | Pancholy |
| 2015/0018869 A1 | 1/2015 | Benz et al. |
| 2015/0032149 A1 | 1/2015 | Croushorn et al. |
| 2015/0164436 A1 | 6/2015 | Maron et al. |
| 2015/0201948 A1 | 7/2015 | Kornowski et al. |
| 2015/0314074 A1 | 11/2015 | Howlett et al. |
| 2015/0327870 A1* | 11/2015 | Fortson .............. A61B 17/0057 606/202 |
| 2015/0327871 A1 | 11/2015 | Fortson et al. |
| 2016/0058988 A1 | 3/2016 | Kesten et al. |
| 2016/0183951 A1 | 6/2016 | Pancholy |
| 2017/0007801 A1 | 1/2017 | Weerakoon et al. |
| 2017/0273693 A1 | 9/2017 | Morrison et al. |
| 2018/0000494 A1 | 1/2018 | Wada et al. |
| 2018/0008281 A1 | 1/2018 | Hazama |
| 2018/0008282 A1 | 1/2018 | Hazama et al. |
| 2018/0008283 A1 | 1/2018 | Hazama |
| 2018/0014832 A1 | 1/2018 | Lampropoulos et al. |
| 2018/0028195 A1 | 2/2018 | Benz et al. |
| 2018/0042615 A1 | 2/2018 | Kimura et al. |
| 2018/0070956 A1 | 3/2018 | Lampropoulos et al. |
| 2018/0185032 A1 | 7/2018 | Matsushita et al. |
| 2018/0250017 A1 | 9/2018 | Matsushita et al. |
| 2018/0280008 A1 | 10/2018 | Okamura |
| 2019/0021742 A1 | 1/2019 | Hazama |
| 2019/0029693 A1 | 1/2019 | Okamura |
| 2019/0046214 A1 | 2/2019 | Hazama |
| 2019/0090886 A1 | 3/2019 | Brown et al. |
| 2019/0133602 A1 | 5/2019 | Kiemeneij et al. |
| 2019/0133604 A1 | 5/2019 | Maeda et al. |
| 2019/0133605 A1 | 5/2019 | Hazama et al. |
| 2019/0133606 A1 | 5/2019 | Hazama |
| 2019/0133607 A1 | 5/2019 | Hazama |
| 2019/0150938 A1 | 5/2019 | Hazama et al. |
| 2019/0167273 A1 | 6/2019 | Morrison et al. |
| 2019/0274692 A1 | 9/2019 | Lampropoulos et al. |
| 2020/0029946 A1 | 1/2020 | Green et al. |
| 2021/0052282 A1 | 2/2021 | Lampropoulos et al. |
| 2022/0047272 A1 | 2/2022 | Hopkinson et al. |

FOREIGN PATENT DOCUMENTS

| | | |
|---|---|---|
| CN | 208864401 | 5/2019 |
| CN | 209695299 | 11/2019 |
| DE | 1006696 | 11/1990 |
| FR | 2828231 | 2/2003 |
| GB | 2109239 | 6/1983 |
| JP | 2012010823 | 1/2012 |
| JP | 2013111444 | 6/2013 |
| JP | 6211285 | 10/2014 |
| JP | 2014200308 | 10/2014 |
| JP | 6261368 | 8/2015 |
| JP | 2015150298 | 8/2015 |
| JP | 6389510 | 9/2015 |
| JP | 6261420 | 11/2015 |
| JP | 2015188608 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019058498 | 4/2019 |
| JP | 2019154915 | 9/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| JP | 6667234 | 2/2020 |
| JP | 202018686 | 2/2020 |
| JP | 202022679 | 2/2020 |
| JP | 202039815 | 3/2020 |
| JP | 202039816 | 3/2020 |
| WO | 199855072 | 12/1998 |
| WO | 2004041313 | 5/2004 |
| WO | 2016118695 | 7/2016 |
| WO | 2017043536 | 3/2017 |
| WO | 2015141786 | 4/2017 |
| WO | 2018017365 | 1/2018 |

OTHER PUBLICATIONS

Pua, et al.,"Snuffbox" Distal Radial Access, J Vasc Interv Radiol, No. 29:44 ,2018.

Zhou, et al., Transient Ulnar Artery Compression Facilitates Transradial Access, Medicine, No. 95:48 ,2016.

European Search Report dated Sep. 7, 2017 for EP 09763115.4.

International Search Report and Written Opinion dated Nov. 28, 2017 for PCT/US2017/041726.

International Search Report and Written Opinion dated Dec. 26, 2017 for PCT/US2017/051715.

International Search Report dated Nov. 18, 2009 for PCT/US2009/042868.

Medplus, Inc , Tourniquet (Radial Artery Compression Device), http://www.bikudo.com/product_search/details/187473/tourniquet_radial_artey_compression_device.html Nov. 24, 2009.

(56) References Cited

OTHER PUBLICATIONS

Notice of Allowance dated Jun. 9, 2014 for U.S. Appl. No. 13/741,046.
Notice of Allowance dated Oct. 16, 2012 for U.S. Appl. No. 12/435,227.
Office Action dated Jan. 10, 2019 for U.S. Appl. No. 15/705,759.
Office Action dated Feb. 14, 2014 for U.S. Appl. No. 13/741,046.
Office Action dated Mar. 2, 2011 for U.S. Appl. No. 12/349,405.
Office Action dated Mar. 5, 2013 for U.S. Appl. No. 13/741,046.
Office Action dated Jun. 6, 2016 for U.S. Appl. No. 14/033,177.
Office Action dated Jun. 28, 2011 for U.S. Appl. No. 12/349,405.
Office Action dated Aug. 17, 2012 for U.S. Appl. No. 12/349,405.
Office Action dated Nov. 3, 2015 for U.S. Appl. No. 14/033,177.
Office Action dated Dec. 8, 2011 for U.S. Appl. No. 12/349,405.
Office Action dated Dec. 27, 2016 for U.S. Appl. No. 14/033,177.
International Search Report and Written Opinion dated Apr. 2, 2019 for PCT/US2018/060089.
Office Action dated May 28, 2019 for U.S. Appl. No. 15/648,110.
Office Action dated Sep. 6, 2019 for U.S. Appl. No. 15/705,759.
Office Action dated Jan. 8, 2020 for U.S. Appl. No. 15/648,110.
Notice of Allowance dated Nov. 25, 2020 for U.S. Appl. No. 29/653,828.
Office Action dated Oct. 8, 2020 for U.S. Appl. No. 16/179,257.
Merit Medical Adds 2 New Products for Assisting Hemostasis, Posted at Merit.com, no posting date, retrieved Aug. 26, 2020 online https://www.merit.com/articles/merit-medical-adds-2-new-products-assisting-hemostasis (2020).
Office Action dated Apr. 12, 2021 for U.S. Appl. No. 16/179,257.
European Search Report dated Feb. 27, 2020 for EP17851579.7.
European Search Report dated Apr. 23, 2021 for EP18872642.6.
European Search Report dated Jul. 9, 2021 for EP18876110.0.
European Search Report dated Nov. 23, 2021 for EP19784978.9.
Extended European Search Report dated Oct. 28, 2021 for EP19763606.1.
International Search Report and Written Opinion dated May 14, 2019 for PCT/US2018/058992.
International Search Report and Written Opinion dated Jun. 12, 2019 for PCT/US2019/020980.
International Search Report and Written Opinion dated Nov. 30, 2021 for PCT/US2021/045607.
Notice of Allowance dated Feb. 3, 2022 for U.S. Appl. No. 16/921,343.
Notice of Allowance dated Sep. 9, 2021 for U.S. Appl. No. 16/294,020.
Notice of Allowance dated Nov. 22, 2021 for U.S. Appl. No. 16/179,257.
Office Action dated May 10, 2021 for U.S. Appl. No. 16/294,020.
Office Action dated Jul. 23, 2021 for U.S. Appl. No. 16/179,257.
Office Action dated Sep. 14, 2021 for U.S. Appl. No. 16/921,343.

* cited by examiner

INFLATABLE COMPRESSION DEVICE

RELATED APPLICATIONS

This application claims priority to U.S. Provisional Application No. 62/656,242, filed on Apr. 11, 2018 and titled, "Inflatable Compression Device," which is hereby incorporated by reference in its entirety.

TECHNICAL FIELD

The present disclosure relates generally to the field of medical devices used to provide hemostasis at a vascular access puncture site. More particularly, some embodiments of the present disclosure relate to inflatable hemostasis devices used to provide hemostasis of the arteries of the wrist, hand and foot, including the distal radial artery, following vascular access. Alignment indicia associated with inflatable hemostasis devices and the use thereof are also disclosed herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
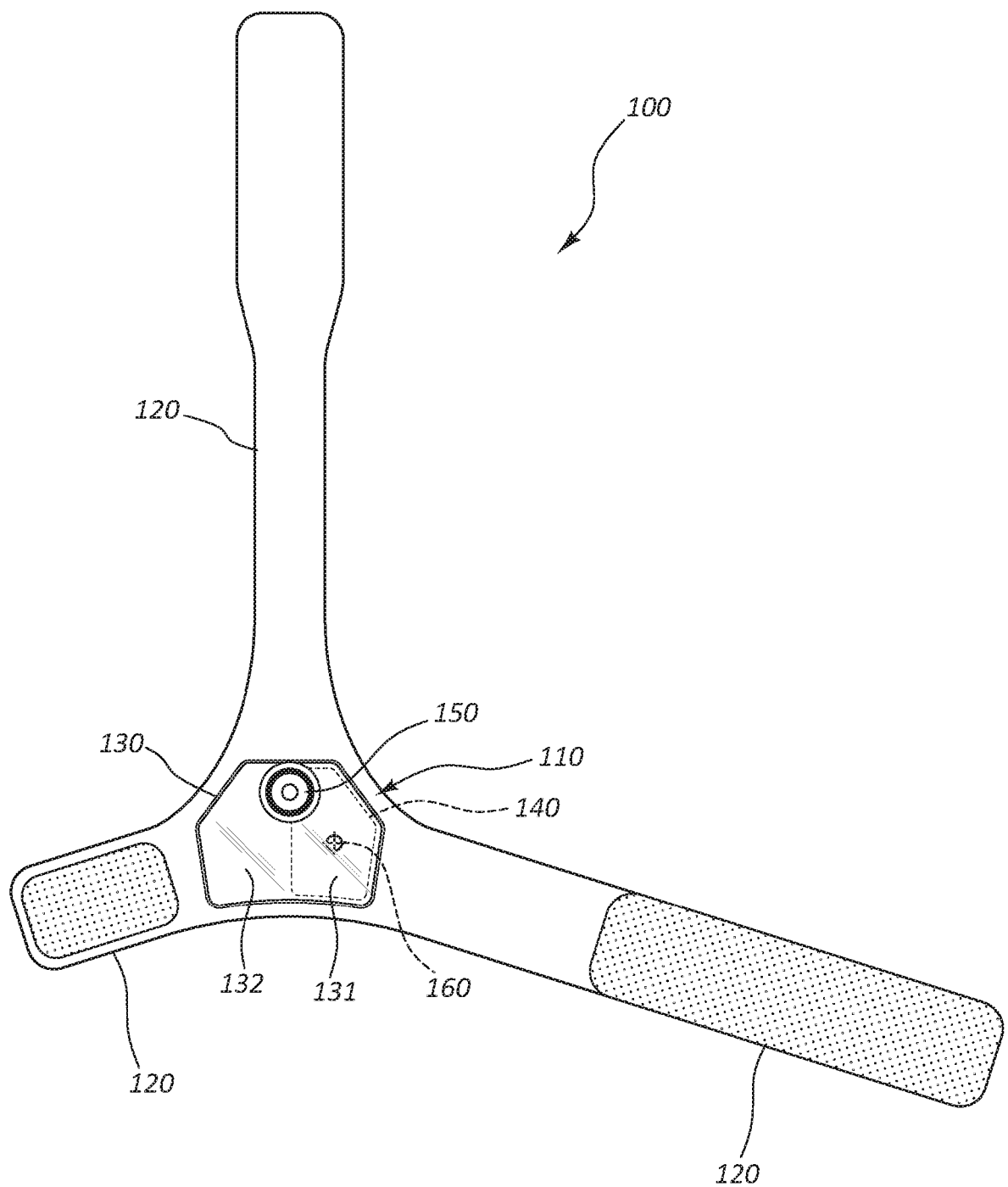
FIG. 1 is a top view of a first inflatable hemostasis device.

In some instances, medical procedures involve insertion of one or more elongate medical devices into the vasculature of a patient. Achieving hemostasis during and/or after an interventional procedure that involves puncturing an artery may present certain challenges. To facilitate hemostasis at an access site, pressure may be applied at or slightly upstream of the skin puncture site. Such pressure may prevent or reduce the leakage of blood from the arteriotomy site and promote hemostasis. The compression may be applied by a healthcare worker or by a hemostasis device, such as the hemostasis devices described herein. In some instances, hemostasis devices may comprise bands for securement of the device to a patient and a compression member to apply a pressure or compressive force to the puncture site.

In some instances, a method for applying compression to a puncture site is through an inflatable hemostasis device. An inflatable hemostasis device may comprise a transparent portion to facilitate alignment of the device and/or visual assessment of hemostasis. An inflatable hemostasis device may also comprise alignment indicia to facilitate alignment of an inflatable bladder over the puncture site. Depending on the location of the alignment indicia on the device, the effects of parallax may affect the ability of the practitioner to properly align the inflatable hemostasis device over the puncture site. The inflatable hemostasis device may be configured to reduce or limit the effects of parallax.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic. Thus, two components may be coupled to each other even though they are not in direct contact with each other. The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

The term "fluid" is used in its broadest sense, to refer to any fluid, including both liquids and gases as well as solutions, compounds, suspensions, etc., which generally behave as fluids.

The term "compression" is used to define a compressive force or pressure applied to a portion of patient over a specific area. The compression level may correlate to a pressure within an inflatable component of the device. The compression level may also correlate to a volumetric size or shape of an inflatable component.

The term "inflation" is defined as a volumetric condition of an expandable sealed container. An increase of inflation is analogous to an increase in fluid content with the container or to the volumetric size of an expandable container. The inflation fluid may be compressible or non-compressible. The inflation level may be may or may not be analogous to an internal pressure.

FIG. 1 provides a top view of an embodiment of an inflatable hemostasis device 100. The hemostasis device 100 may comprise a compression member 110 and a securement system 120. The securement system 120 may be coupled to the compression member 110 and be configured to facilitate a secure attachment of the compression member 110 over a puncture site. The hemostasis device 100 may be configured to provide compression to various locations on a patient and the securement system may be configured to secure the hemostasis device 100 to various portions of a patient's body such as a wrist, hand or foot.

The securement system 120 may comprise bands that wrap around a portion of the patient's body. There may be one, two, three, four or more bands. The bands may comprise any suitable releasable securement mechanism, such as a hook-and-loop material, pressure sensitive adhesives, buckles, magnets, snaps, clasps, etc. all of which are contemplated to be within the scope of this disclosure. The securement system 120 may be configured to provide lateral and longitudinal positional stability of the compression member 110 over a puncture site.

As stated above the hemostasis device 100 may comprise a compression member 110. As illustrated in FIG. 1, the compression member 110 is specifically configured to provide compression to the snuff box of the left hand. However, the compression member 110, as described herein, may be considered generic. Said another way, the compression member 110 may be configured to provide compression to various locations on a patient such as a wrist, hand or foot.

The compression member 110 may be configured to provide compression over a specifically defined area of a patient. The compression member 110 may comprise a perimeter 115 of FIG. 2A having a plurality of sides. There may be three, four, five, six or more sides. The sides may be straight, concave or convex. The sides may be configured to facilitate coupling of the securement system 120 to any number of sides. The compression member 110 may comprise a symmetrical or non-symmetrical shape. The shape may be configured to correlate with the anatomy of a patient adjacent a puncture site. The shape may also facilitate proper alignment and placement of the hemostasis device 100. Still again, the shape may facilitate desired aesthetic properties of the hemostasis device 100. The compression member 110 may comprise components that are transparent or translucent.

Figure 2A:
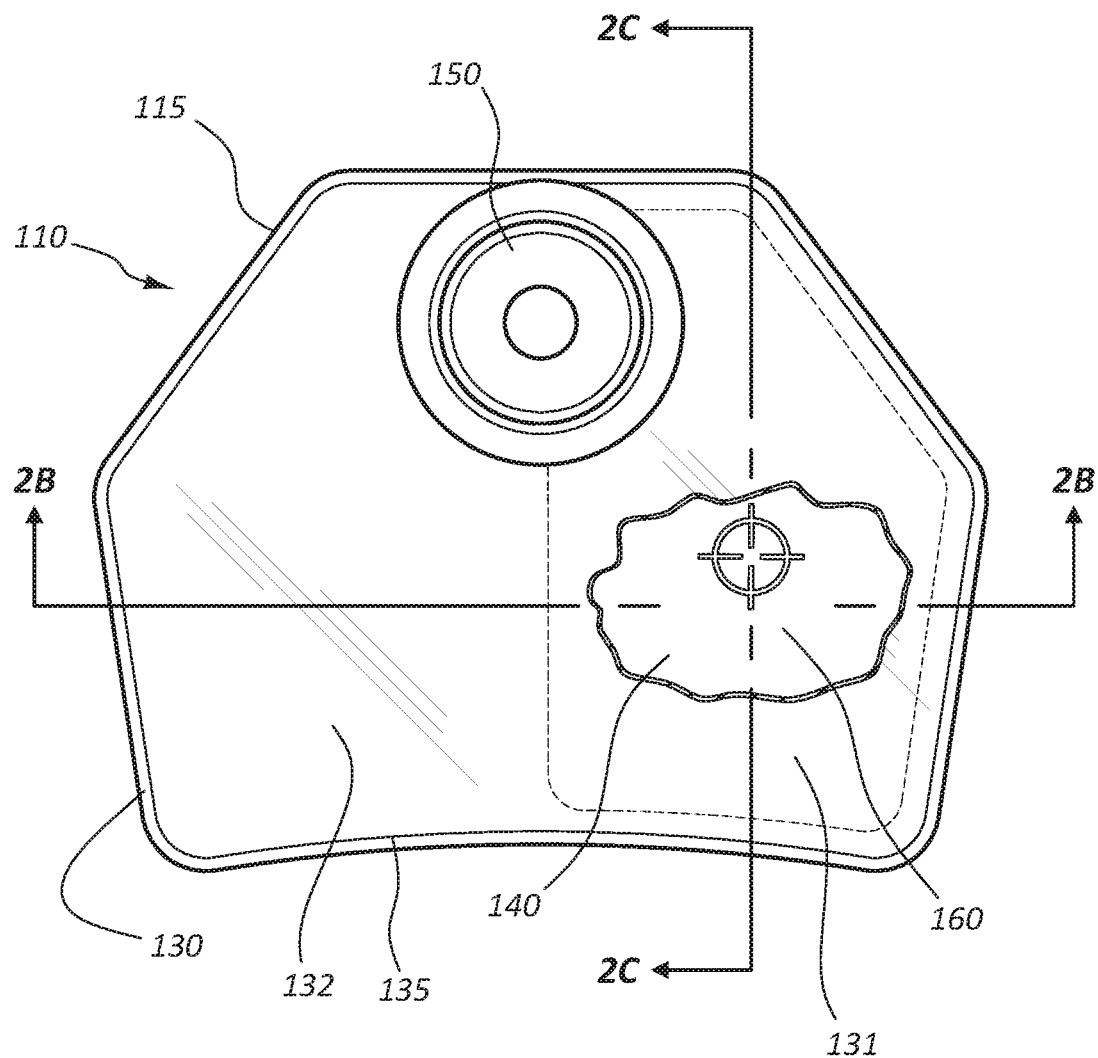
FIG. 2A is a top view of a compression member of the inflatable hemostasis device of FIG. 1 with a portion of a compression member sectioned away.

FIG. 2A shows the compression member 110 having properties, features and characteristics consistent with the hemostasis device 100. However, one of ordinary skill in the art having the benefit of this disclosure will understand that certain properties, features, and characteristics described herein are generic in nature and may apply to hemostasis devices configured to provide compression to any location on a patient and for any therapy where compression is beneficial.

As illustrated in FIGS. 1 and 2A, the compression member 110 may comprise a top plate 130, a bladder 140, an inflation port 150, and a location indicium 160. The bladder 140 may be disposed on the bottom of the compression member 110 so as to be disposed adjacent the skin of a patient and provide compression to a puncture site. The bladder 140 may be coupled to the top plate 130 and in fluid communication with the inflation port 150. The location indicium 160 may be disposed at any suitable location on the compression member 110.

Figure 2B:
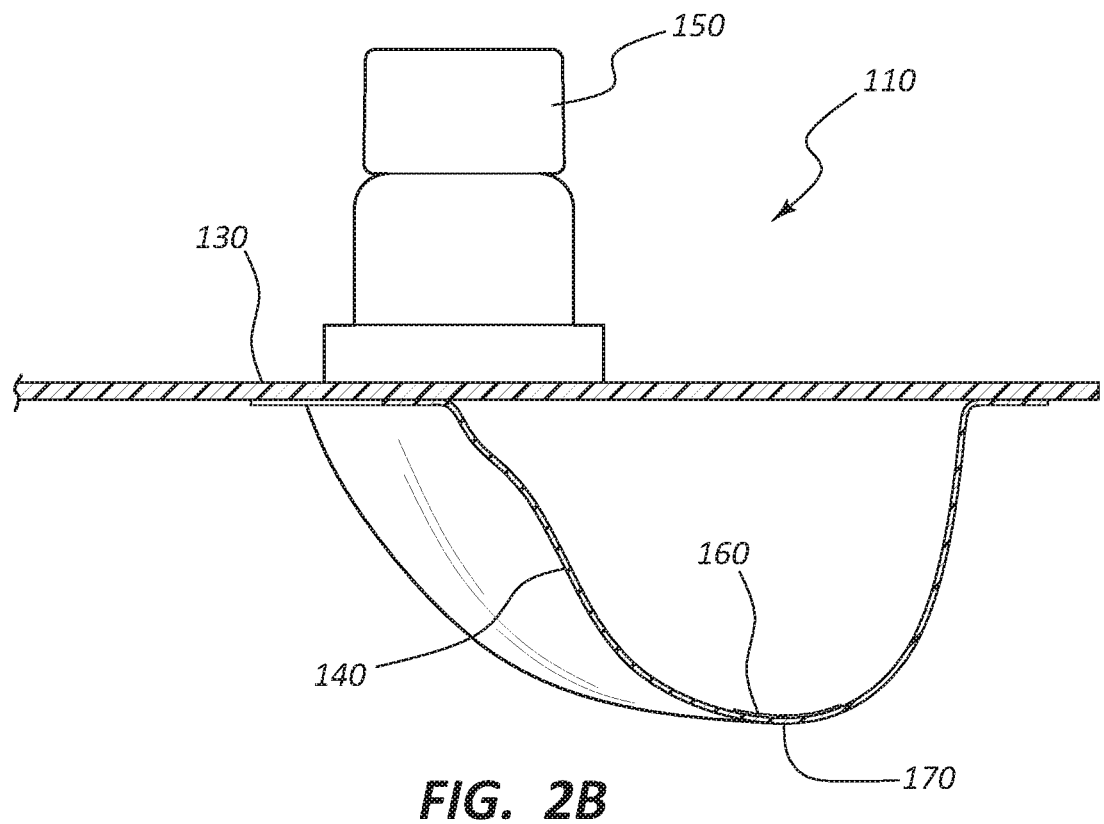
FIG. 2B is a cross-sectional side view of the compression member of FIG. 2A through section line 2B-2B.
Figure 2C:
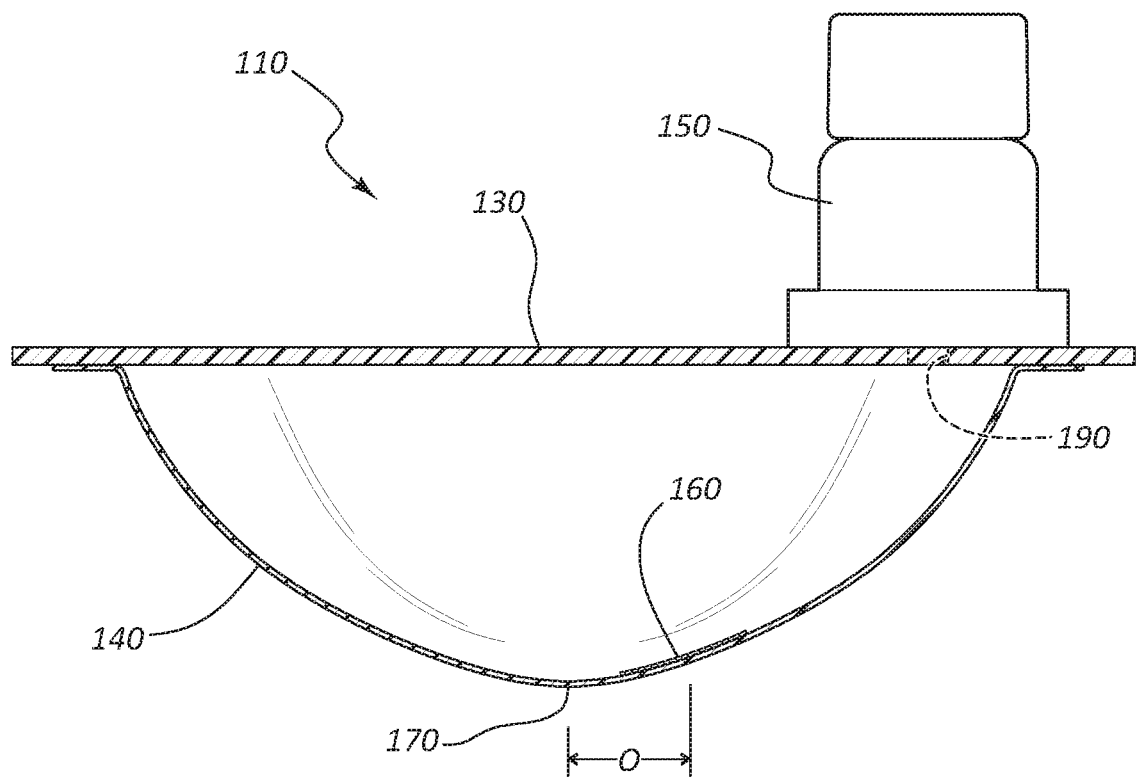
FIG. 2C is a cross-sectional side view of the compression member of FIG. 2A through section line 2C-2C which is orthogonal to section line 2B-2B of FIG. 2B.

Referring now to FIGS. 2A-2C, the top plate 130 may be configured to convert tension in the securement system 120 to a downward force on the patient. The top plate 130 may be configured to provide a support for the bladder 140. The top plate 130 may be flexible or semi-flexible so as to conform to the anatomy of a patient upon securement. The top plate 130 may also be rigid. The top plate 130 may comprise a substantially flat plate, and/or may comprise flat, curved, convex or concave portions. Further, the top plate 130 may be symmetrical or non-symmetrical. In the illustrated embodiment, the top plate 130 is coupled to the securement system 120. The top plate 130 may comprise a perimeter 135 having a plurality of sides. There may be three, four, five, six or more sides. The sides may be straight, concave or convex. The sides may be configured to facilitate coupling of the securement system 120 to any number of sides. The top plate 130 may comprise at least one of a hole, slot, protrusion, etc. to facilitate coupling to the securement system 120.

The top plate 130 may be configured to be anatomically compatible with a patient, such as avoiding uncomfortable contact points. The top plate 130 may also be configured to provide some level of compression without inflation of the bladder 140 such as comprising a convex portion on the bottom side thereof. The top plate 130 may comprise a compression portion 131 disposed above the bladder 140 and a non-compression portion 132. In some embodiments, the compression portion 131 may comprise the entire top plate 130. Additionally, in some embodiments, the non-compression portion 132 may comprise a viewing window through which a practitioner may visually observe at least a portion of the puncture site.

A bottom surface of the top plate 130 may comprise features such as protrusions, surface displacements, variations in thickness, position or alignment indicators, surface texturing, etc. to facilitate welding or bonding of the bladder 140 to the top plate 130. A top surface of the top plate 130 may comprise features such as protrusions, surface displacements, variations in thickness, position or alignment indicators, surface texturing, etc. to facilitate welding or bonding of the inflation port 150 to the top plate 130. The top plate 130 may comprise an orifice 190 extending through the top plate 130.

The top plate 130 may be transparent or translucent such that the puncture site can be seen through the top plate 130 to facilitate alignment of the compression member 110 with the puncture site and assessment of hemostasis during treatment. The top plate 130 may be formed of any suitable flexible or semi-flexible material such as polyethylene, polypropylene, polyvinyl chloride, polyurethane, etc. or any suitable rigid material, such as polycarbonate, polystyrene, styrene copolymers, polyethylene terephthalate, acrylic, polyethylene, polypropylene, etc.

Referring again to FIGS. 2A-2C, the bladder 140 may be configured to extend downward from the top plate 130 upon inflation. The bladder 140 may be disposed on the bottom surface of the top plate 130 such that the top plate 130 prevents upward expansion of the bladder 140. The bladder 140 may be configured to be in contact with a patient's skin and provide compression to a puncture site of a patient. The bladder 140 may be configured to contain a fluid and maintain an internal fluid pressure. The bladder 140 may be configured so that an internal fluid pressure within the bladder 140 and the compressive pressure applied to a patient over a specified area are equal or substantially equal. The bladder 140 may be configured to be inflatable and deflatable. The bladder 140 may be configured to provide compression to a puncture site over a predefined area or shape. The bladder may be configured to provide a predefined compression depth profile. In some circumstances, the compression area on a patient may be relatively large or small and the compression profile may be relatively deep or shallow defining a range of volumetric capacities for the bladder 140. For example, in some embodiments, the maximum capacity of the bladder 140 may be between 3 mL and 12 mL, between 3 mL and 20 mL, or between 3 mL and 25 mL. In another embodiment, the maximum capacity may be between 5 mL and 15 mL, between 10 mL and 20 mL, between 10 mL and 30 mL, or between 15 mL and 30 mL.

The bladder 140 may comprise a flat sheet or a preformed 3-dimensional shape. The bladder 140 may be flexible and non-stretchable or flexible and stretchable. The bladder 140 may be transparent or translucent to facilitate visible observation of a puncture site. The bladder 140 may be coupled to the top plate 130. The bladder 140 may be sealably coupled to the top plate 130 along a perimeter of the bladder 140 such that a portion of the top plate 130 forms a top wall of the bladder 140. The orifice 190 may be deposed within the perimeter of the bladder 140.

The bladder 140 may be configured to define specific compression characteristics. Such characteristics may comprise the area, depth, and shape of the compression on a patient. FIGS. 2B and 2C show orthogonal cross-sectional views of the compression member 110 with cut lines through an apex 170 of the bladder 140 when the bladder 140 is inflated. The apex 170 is defined as the point on the bladder 140 most distant from the top plate 120 when the bladder 140 is inflated. As illustrated, the bladder 140, when inflated, defines a compression profile or volumetric shape. When inflated there may be an apex 170 of the bladder 140. The location of the apex 170 may be centered within the perimeter of the bladder 140. The location of the apex 170 may be offset from the center of the bladder 140. The location of the apex 170 may be predetermined by the characteristics of a preform of the bladder 140. Such characteristics may comprise thickness variation and/or three-dimensional shape. The bladder 140 may comprise a thick portion to facilitate a relatively flat or uniform compression area on a patient. The bladder 140 may comprise preformed folds, such as a bellows arrangement, to facilitate a predefined compression depth and/or profile. The preform of the bladder 140 may also facilitate the manufacturing processes of the compression member 110, e.g. printing of an indicium 160 on an inner surface of the bladder 140. The preform of the bladder 140 may also facilitate a desired position of the indicium 160 relative to a perimeter of the top plate 130 when the bladder 140 is in an uninflated state. The bladder 140 may be formed from any suitable, flexible, transparent or translucent material, such as polyethylene, polypropylene, polyurethane, etc.

Referring again to FIGS. 2A-2C, the inflation port 150 may be in fluid communication with the bladder 140. The inflation port 150 may be coupled to the top plate 130 such that the inflation port 150 is in fluid communication with the orifice 190. As such, fluid communication between the inflation port 150 and the bladder 140 may comprise the orifice 190. The inflation port 150 may be disposed toward an outer perimeter of the bladder 140 such that the inflation port 150 does not obstruct visualization of the puncture site. The inflation port 150 may be disposed on a line bisecting the top plate 130. FIGS. 2A-2C show the inflation port 150 oriented perpendicular to the top plate 130. However, the inflation port 150 may be coupled at any angle relative to an axis perpendicular to the top plate 130. The inflation port 150 may comprise a valve to provide for inflation and deflation of the bladder 140 and containment of fluid pressure within the bladder 140. The inflation port 150 may be configured to be releasably coupleable to a fluid displacement device, such as a syringe.

Figure 3:
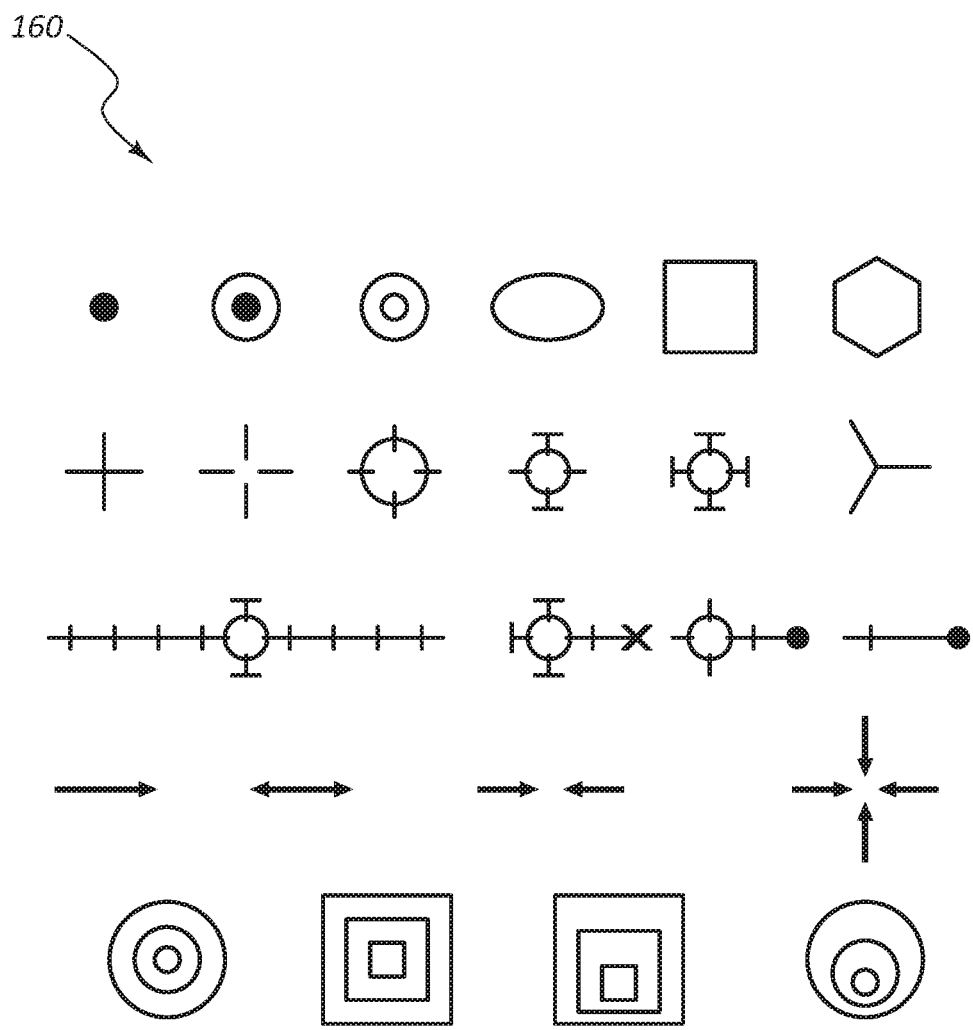
FIG. 3 is an illustration of several embodiments of a location indicium.

FIG. 3 shows several potential embodiments of patterns for the location indicium 160. The illustration of FIG. 3 is non-inclusive and any and all other indicia comprising dots, line segments, curves, circles, polygons, contour lines, arrows, crosses, etc. and any combination thereof that may be configured for alignment purposes are within the scope of this disclosure. The location indicium 160 may comprise a point component so as to facilitate two-dimensional alignment of the compression member 110 on the puncture site. The indicium 160 may comprise at least one linear component to facilitate rotational alignment with a linear aspect of the patient such as an artery. Additionally or alternatively, the indicium 160 may comprise at least one directional component such as an arrow. The directional component may be used to rotationally align the compression member 110 with a specific directional aspect of a patient such as blood flow direction through an artery. The location indicium 160 may comprise one, two or all three components of alignment as described above. Additional location indicia may also be disposed on the compression member 110 and may comprise one, two or all three components of alignment as described above.

The location indicium 160 may also indicate an area, shape and/or depth profile of the compression applied to the patient. The location indicium 160 may also comprise contour lines or other components to indicate a concentric or non-concentric depth profile.

The location indicium 160 may comprise a sequence of two or more components. The sequence may define one or more predetermined distances or lengths, such as graduation marks. The sequence of two or more components may correlate with multiple point locations on a patient, such as a skin puncture site and an arteriotomy site.

The location indicium 160 may be disposed on the bladder 140. In some embodiments, the location indicium 160 may be disposed on an inner surface of the bladder 140 as shown in FIGS. 2B and 2C. Disposition of the location indicium 160 on the inner surface of the bladder 140 may provide protection from being inadvertently removed or otherwise damaged through physical contact and/or chemical contact, e.g. with cleaning agents. The patient may also be protected from contact with the location indicium 160 such as printing chemicals, surface roughness, etc.

The location indicium 160 may be disposed adjacent a center location of the bladder 140. The location indicium 160 may be disposed adjacent the apex 170 of the bladder 140. The location indicium 160 may be disposed a distance O offset from the center and/or the apex 170 of the bladder 140 as shown in FIG. 2C. The offset distance may correlate to the distance between the skin puncture site and the arteriotomy site or may correlate to other marks on a patient's skin.

Alignment of the compression member 110 with the puncture site on a patient may facilitate hemostasis. Alignment may be facilitated by viewing the puncture site through a transparent or translucent top plate 130 and/or bladder 140. Alignment may be further facilitated by visually aligning the location indicium 160 with the puncture site. In some instances, aligning the location indicium 160 disposed on the compression member 110 with a puncture site on a patient may need to take into account parallax.

Figure 4:
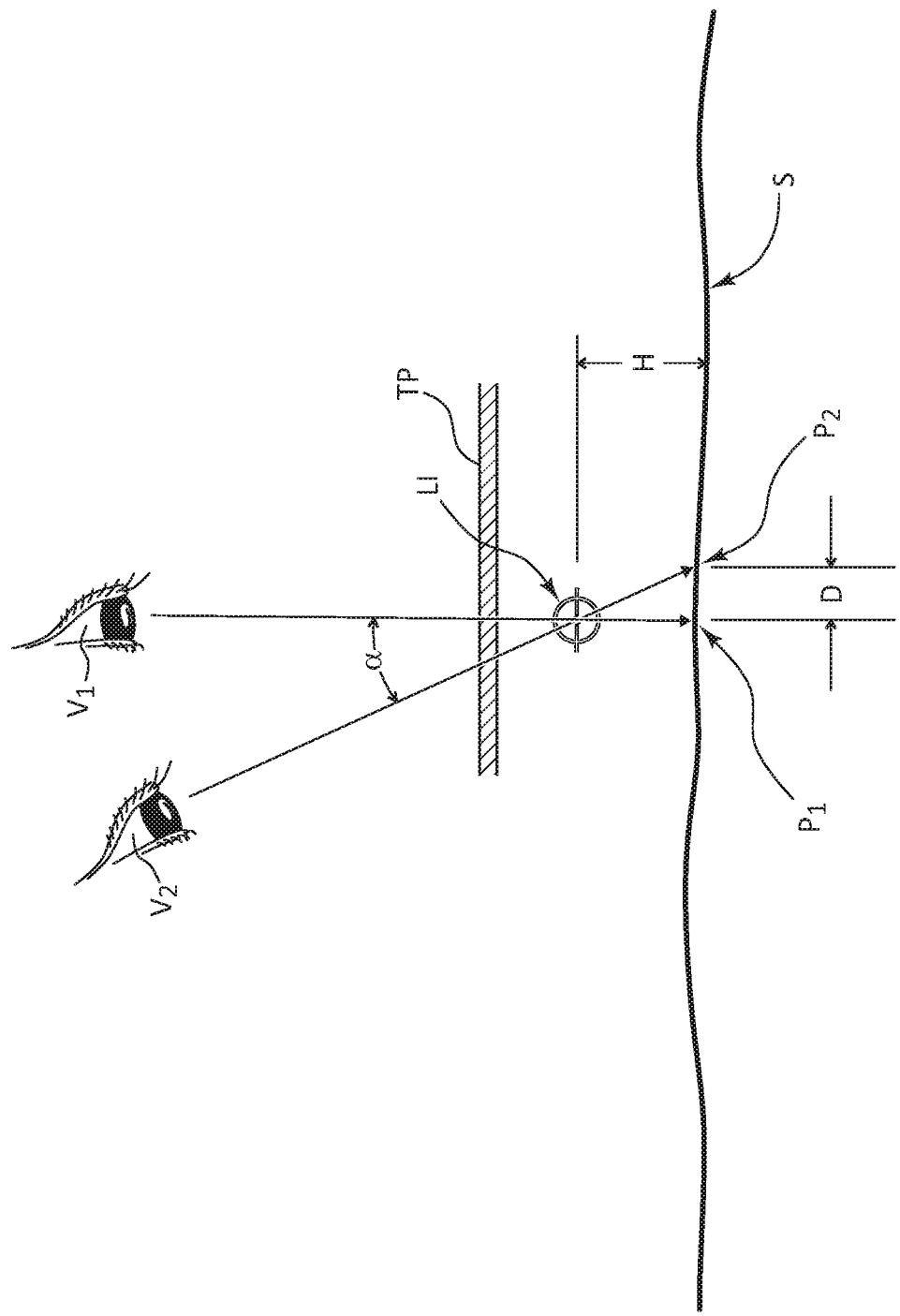
FIG. 4 is an illustration of the parallax effect as may be encountered during alignment of the hemostasis device of FIG. 1 over a puncture site.

FIG. 4. illustrates the effects of parallax as may be applicable to inflatable hemostasis devices. A location indicium LI is shown disposed a height H above the skin surface S of a patient. A normal viewing position V1, i.e. normal to a top plate TP, defines a projected indicium location P1 on the skin surface S. A second viewing position V2, angularly offset from V1 by an angle α, defines a second projected indicium location P2 on the skin surface S. The distance D between P1 and P2 may be approximated by the equation D=H×Tangent(α). Patient anatomy, position of the puncture site and patient movement may all contribute to a wide variation in viewing angles α relative to an axis normal to the top plate TP. The location indicium LI may also be disposed at a significant height H above the skin surface S. These two factors may result in misalignment of the indicium LI relative to a puncture site on a patient even when alignment may visually appear to be correct. For example, an angular difference α of 45 degrees and a height H of 3 mm may combine to produce a distance D approaching 3 mm between the two projected indicium locations P1, P2 on the skin S. In some instances, a miss-alignment distance may cause insufficient compression to a puncture site. Hence, a reduction in the parallax effect may facilitate compression of a puncture site. For a second example, an included angle α of 45 degrees between two viewing positions V1, V2 and a height H of 3 mm may combine to produce a distance D approaching 3 mm between two projected indicium locations P1, P2 on the skin S when neither of the viewing angles are normal to the top plate TP.

The inflatable hemostasis device 100 may be configured to limit the parallax effect (distance D). For example, compression member 110 may be configured to limit the parallax distance D as described above for a viewing angle α of 45 degrees to 5, 4, 3, 2, 1, 0.5, 0.25 mm or less. The parallax effect may be reduced by reducing the height H. In certain instances reducing the height H by disposition of the location indicium 160 on the inner surface of the bladder 140 may reduce the parallax effect. The bladder 140 may be adjacent to or in direct contact with the patient's skin when inflated, thereby positioning the location indicium adjacent the skin. Disposition of the location indicium 160 on the inner surface of the bladder 140, may limit the parallax effect D to be equivalent to the thickness of the bladder 140 when viewed from a 45 degree viewing angle.

In some instances, minimizing the parallax effect when the hemostasis devise 100 is initially placed on the patient so that initial alignment of the indicium 160 with the puncture site is correct may facilitate hemostasis. The bladder 140 may be partially inflated or otherwise configured to be significantly close to or in contact with the skin of the patient upon initial placement of the compression member 110 on the patient. The top plate 130 and/or bladder 140 may be configured to dispose the bladder 140 close to or in contact with the skin of the patient when uninflated.

Figure 2D:
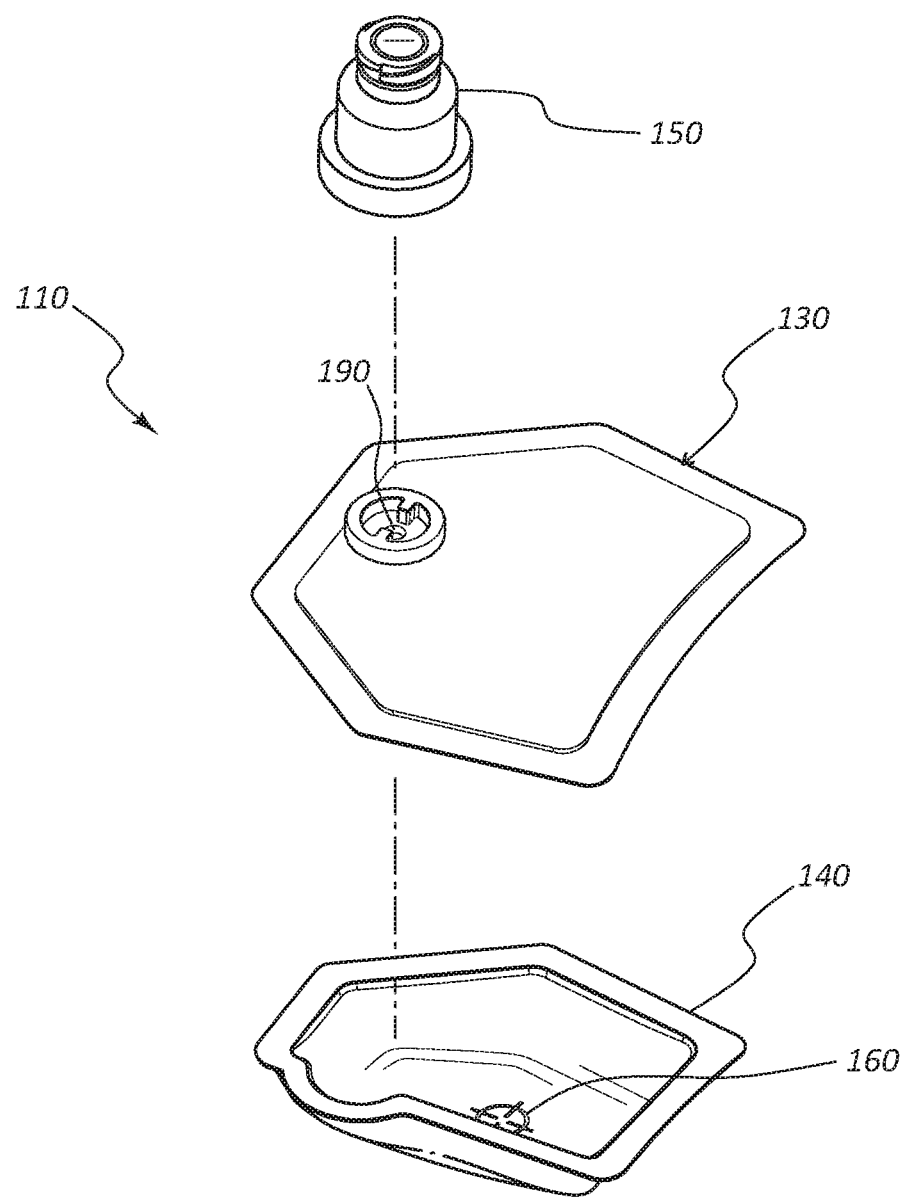
FIG. 2D is an exploded view of the compression member of FIG. 2A

FIG. 2D shows an exploded view of the compression member 110. A manufacturing process of the compression member 110 may comprise sealably coupling the inflation port 150 to the top surface of the top plate 130 and sealably coupling the bladder 140 along the perimeter thereof to the bottom surface of the top plate 130. Methods of coupling inflation port 150 to the top surface of the top plate 130 and the bladder 140 to the bottom surface of the top plate 130 may comprise ultra-sonic welding, radio frequency welding, solvent bonding, boding with adhesives, etc.

The manufacturing process may also comprise placement of the location indicium 160 on the inner surface of the bladder 140 prior to coupling the bladder 140 to the top plate 130. The process of placing the location indicium 160 on the bladder 140 may comprise altering the visible properties of the bladder 140 during or after the forming process of the bladder 140 which altering may comprise the forming of protrusions or recesses, surface texturing, laser marking, chemical etching, heat staking, etc. The process of placing the location indicium 160 on the bladder 140 may comprise adding a visible component, e.g. a label, or a visible substance, e.g. ink, to the inner or outer surface of the bladder 140. The process of applying the location indicium 160 to the bladder 140 may comprise preparing the surface prior to applying the component or substance thereto. Such preparing may comprise wiping the surface with a cleaning or degreasing agent such as isopropyl alcohol, removing static charge, applying a primer, etching or otherwise altering the surface finish, etc. The process of adding a visible substance may comprise pad printing, ink jet printing, screen printing, laser marking, UV marking, thermal transfer printing, etc.

The process of placing the location indicium 160 on the bladder 140 may comprise initially determining the position for the location indicium 160 on the bladder 140. The determining process may include identifying the apex 170 of the bladder 140 when inflated and thereafter, using the identified apex 170 as a reference point for the position of the location indicium 160. The positioning of the location indicium 160 relative to the apex 170 may comprise assessment of at least one of the distance between the arteriotomy site and the puncture site, depth of the compression, shape of the bladder 140 when inflated, shape of the preform of the bladder 140, direction of blood flow through an artery, etc.

The manufacturing process of the compression member 110 may also comprise adding or removing fluid from the bladder 140 after coupling the bladder 140 and the inflation port 150 to the top plate 130. The manufacturing process of the inflatable hemostasis device 100 may further comprise coupling the compression member 110 to a securement system 120

Figure 5A:
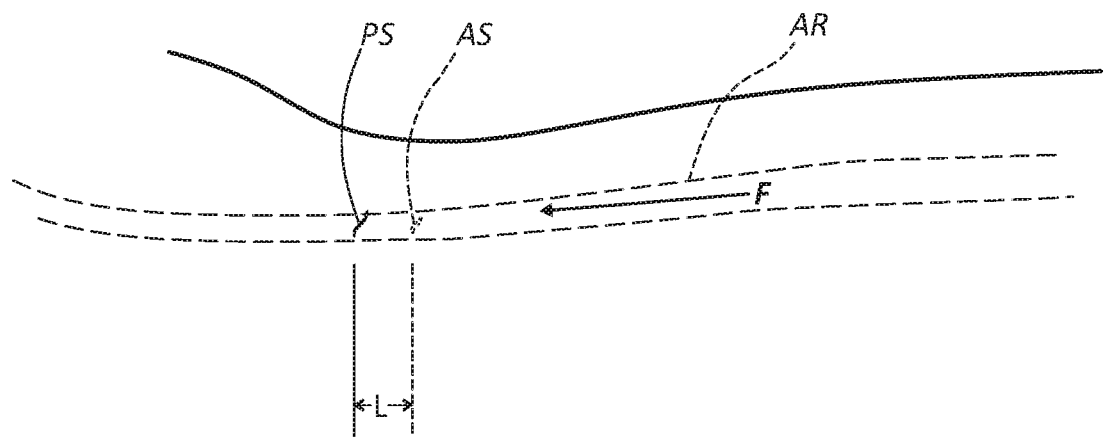
FIG. 5A is a top view of a vascular access site on a portion of a patient.

FIGS. 5A-5D show various stages of the compression member 110 in use. FIG. 5A is a top view of a portion of a patient comprising a vascular access site. FIG. 5A shows a puncture site PS on the skin surface, an artery AR beneath the skin surface, blood flow direction F and an arteriotomy site AS. The arteriotomy site AS is shown at a length L upstream, i.e. opposite the direction of blood flow F, of the skin puncture site PS.

Figure 5B:
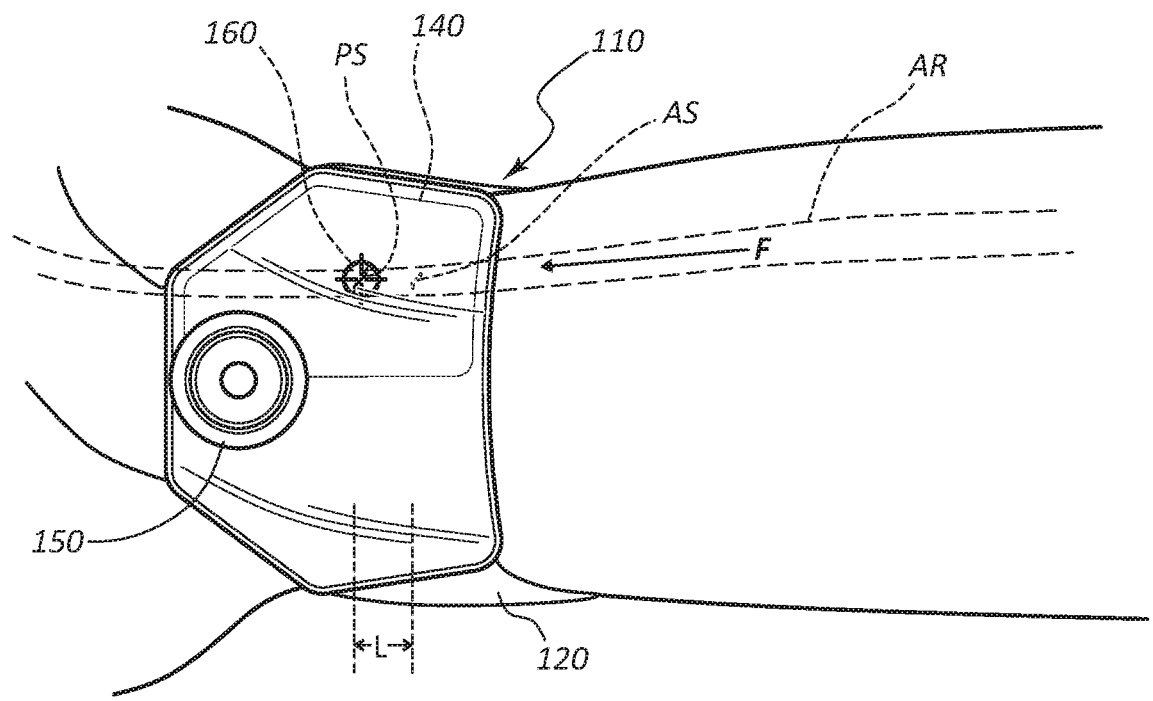
FIG. 5B is a top view of the compression member of FIG. 2A disposed on the vascular access site of FIG. 5A.
Figure 5C:
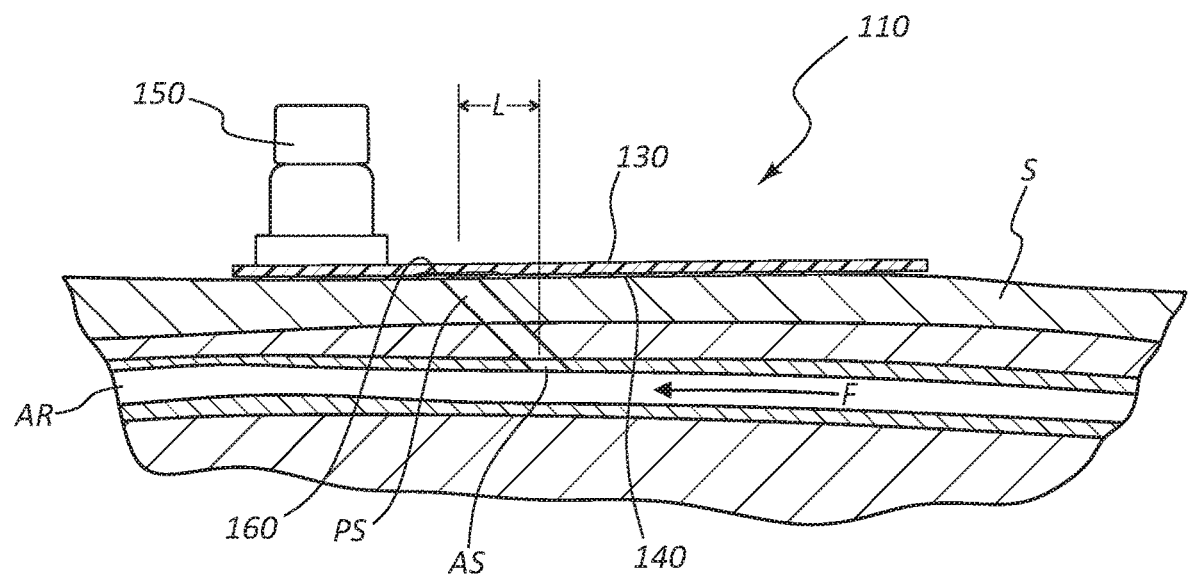
FIG. 5C is a cross-sectional side view of the compression member of FIG. 2A disposed on the vascular access site of FIG. 5A in an uninflated state.
Figure 5D:
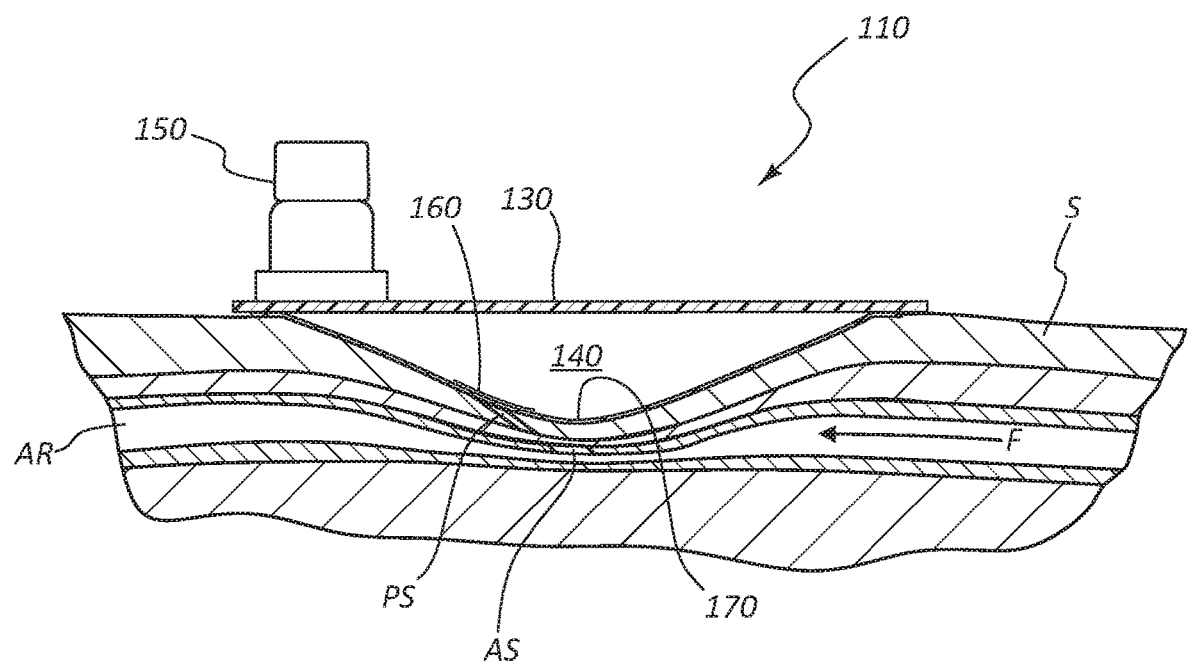
FIG. 5D is a cross-sectional side view of the compression member of FIG. 2A disposed on the vascular access site of FIG. 5A in an inflated state.

FIG. 5B is a top view of the compression member 110 disposed on the portion of a patient shown in FIG. 5A. Inflation port 150 is shown not obstructing the view of the puncture site PS. Also shown is the location indicium 160 aligned adjacent the skin puncture site PS. FIG. 5C is a cross-sectional side view of the illustration of FIG. 5B. FIG. 5C shows an uninflated bladder 140 disposed adjacent the skin surface S and the location indicium 160 aligned adjacent the skin puncture site PS. FIG. 5D shows the illustration of FIG. 5C with the bladder 140 inflated. Compression of the patient's skin and artery AR is shown. The location indicium 160 is shown adjacent the skin puncture site PS and the apex 170 of the inflated bladder 140 is shown adjacent the arteriotomy site AS. In other embodiments, the indicium may extend over both the skin puncture site and the arteriotomy site.

The method of use may comprise the steps or processes described below. A vascular access catheter or needle may be initially present prior to use of the inflatable hemostasis device 100 comprising the compression member 110. The bladder 140 may be initially uninflated, partially inflated, or substantially fully inflated, or the bladder 140 may contain a vacuum. The practitioner may adjust the level of inflation of the bladder 140 prior to placing the compression member 110 on the patient. For example, the practitioner may partially inflate the bladder 140 so that the indicium 160 disposed on the bladder 140 is adjacent the skin of the patient. As illustrated in FIGS. 5B and 5C, the practitioner may place the compression member 110 on the patient and align the location indicium 160 with the skin puncture site PS or the practitioner may align the location indicium 160 offset a predefined distance from the skin puncture site PS. The practitioner may rotationally align the compression member 110 with a longitudinal axis of the artery and the direction of blood flow F. At this stage, the bladder 140 may be uninflated, partially inflated, substantially fully inflated or contain a vacuum. The practitioner may secure the compression member 110 to the patient using the securement system 120 as shown in FIG. 5B. The practitioner may adjust the level of inflation in the bladder 140 after securement so as to prevent bleeding. The practitioner may assess alignment of the compression member 110 after securement and adjust the positional or rotational alignment. The practitioner may adjust the level of inflation of the bladder 140 according to a predetermined protocol or in response to a patient condition such as discomfort, bleeding, etc. Once hemostasis is achieved, the securement system 120 may be disabled and the compression member 110 removed.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Figure 6A:
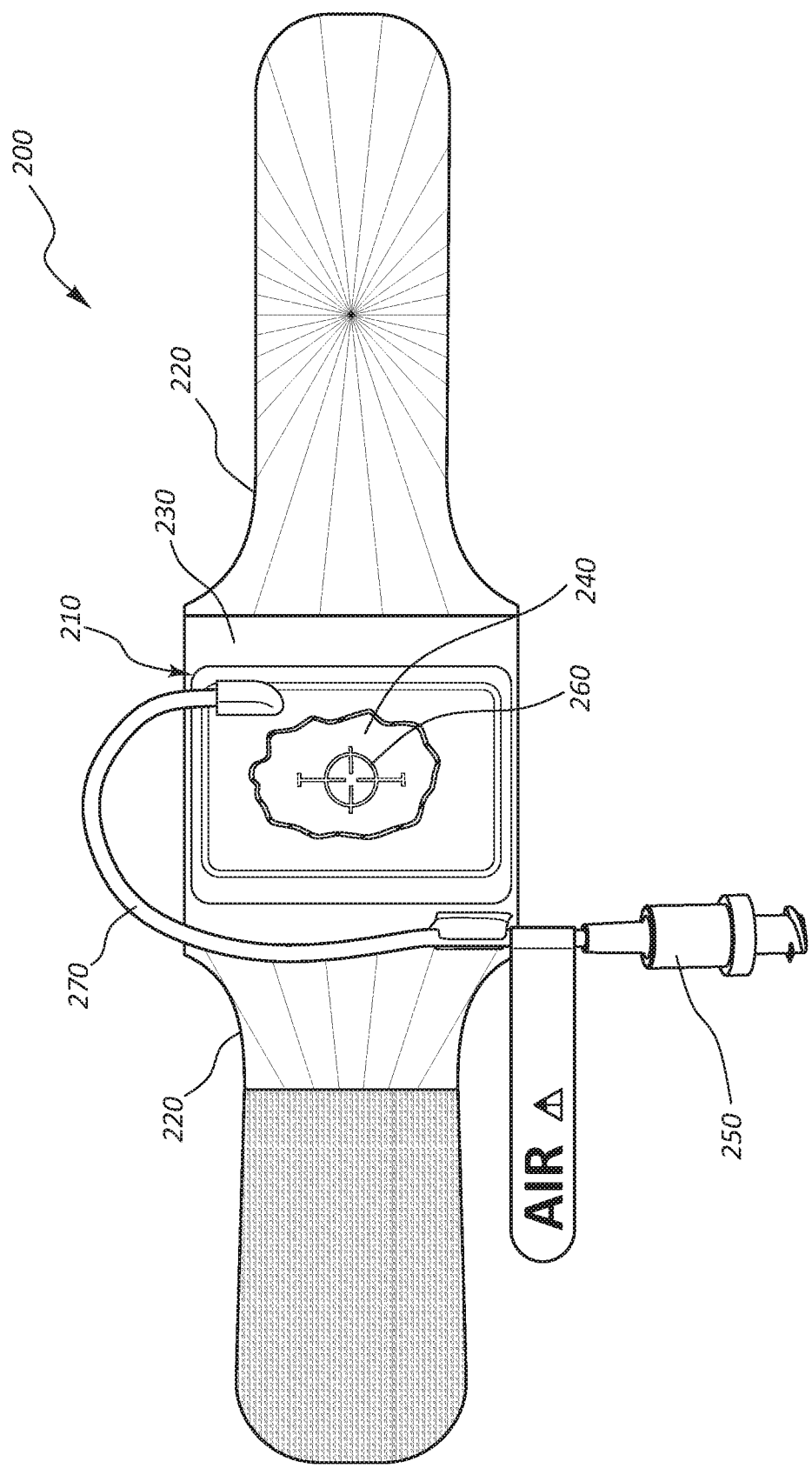
FIG. 6A is a top view of a second inflatable hemostasis device with a portion of a compression member sectioned away.
Figure 6B:
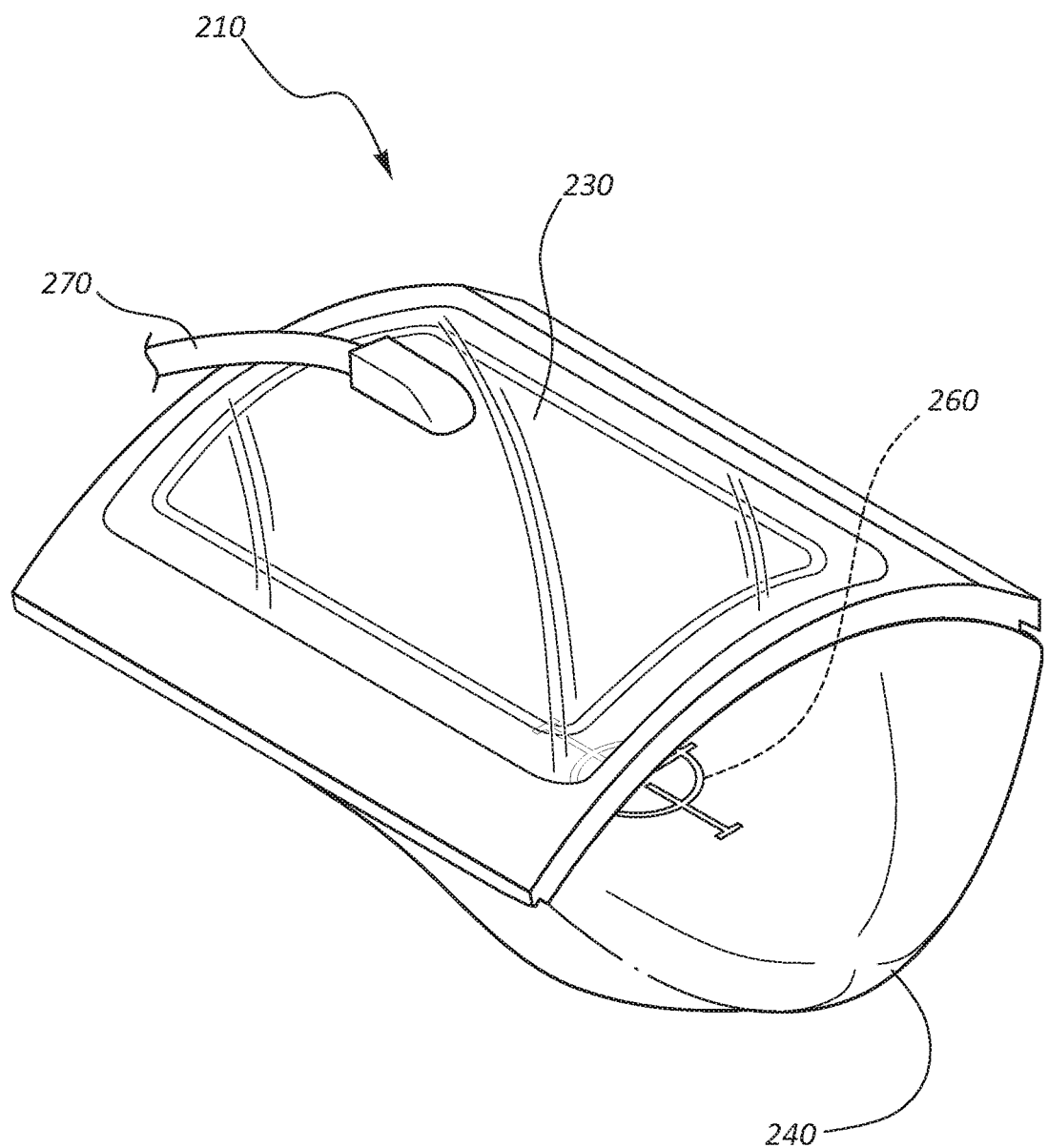
FIG. 6B is a perspective view of a compression member of the inflatable hemostasis device of FIG. 6A.

FIGS. 6A and 6B show a second embodiment of a hemostasis device 200 that resembles the hemostasis device 100 described above in certain respects. Accordingly, like features are designated with like reference numerals, with the leading digits incremented to "2." For example, the embodiment depicted in FIGS. 6A and 6B includes a compression member 210 that may, in some respects, resemble the compression member 110 of FIGS. 1 and 2A-2D. Relevant disclosure set forth above regarding similarly identified features thus may not be repeated hereafter. Moreover, specific features of the hemostasis device 100 and related components shown in FIG. 1 may not be shown or identified by a reference numeral in the drawings or specifically discussed in the written description that follows FIGS. 6A and 6B. However, such features may clearly be the same, or substantially the same, as features depicted in other embodiments and/or described with respect to such embodiments. Accordingly, the relevant descriptions of such features apply equally to the features of the hemostasis device 200 and related components depicted in FIGS. 6A and 6B. Any suitable combination of the features, and variations of the same, described with respect to the hemostasis device 100 and related components illustrated in FIGS. 1, 2A-2D can be employed with the hemostasis device 200 and related components of FIGS. 6A and 6B, and vice versa.

FIG. 6A is a top view of a second embodiment of a vascular access hemostasis device 200 configured to provide compression to the radial artery of a patient. The hemostasis device 200 comprises a securement system 220 and a compression member 210. The securement system 220 comprises two bands and may be configured to be secured to the wrist of a patient. The securement system 220 is coupled to the compression member 210. The compression member 210, as shown in FIG. 6A, is specifically configured to provide compression to the radial artery of a patient. However, the compression member 210 as described herein may be considered generic. Said another way, the compression member 210 may be configured to provide compression to other various locations on a patient, such as a wrist, hand, or foot. The compression member 210 may comprise a top plate 230, a bladder 240, an inflation port 250, a location indicium 260, and an inflation tube 270. The top plate 230 is shown partially cut out in FIG. 6A to show the location indicium 260 disposed on an inner surface of the bladder 240. The inflation tube 270 may be in fluid communication with the bladder 240 at one end. The inflation tube 270 may be coupled to and in fluid communication with the inflation port 250 at another end. The inflation tube 270 may also be coupled to the top plate 230 at one or more locations. The inflation tube 270 may in fluid communication with an orifice (not shown) extending through the top plate 230.

FIG. 6B is a perspective view of the compression member 210. The top plate 230 may be rigid and may be non-flat as shown in FIG. 6B The top plate 230 may comprise curvature to fit partially around a patient's wrist or other portion of a patient. The curvature of the top plate 230 may also be configured to provide alignment of the bladder 240 with a puncture site. The bladder 240 is shown in an inflated state. The location indicium 260 as shown may be disposed on an inner surface of the bladder 240.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The invention claimed is:

1. An inflatable hemostasis device, comprising:
   a top plate; and
   a bladder comprising a flexible material sealably coupled to the top plate along a perimeter of the bladder;
   wherein the bladder comprises an apex when inflated and a location indicium disposed directly on the flexible material, the location indicium comprising a first portion linearly offset from the apex and configured to be positioned over a skin puncture site, a second portion disposed at the apex and configured to be positioned over an arteriotomy, and a third portion disposed between the first portion and the second portion and configured to axially align the bladder with an artery; and
   wherein the first portion and the second portion are disposed on an inner surface of the bladder and
   wherein the top plate and the bladder are transparent such that a puncture site is viewable through the top plate and the bladder.

2. The inflatable hemostasis device of claim 1, further comprising an inflatable hemostasis device securement system coupled to the top plate, wherein the securement system is configured to secure the bladder over the puncture site.

3. The inflatable hemostasis device of claim 1, wherein an alignment of the location indicium with the puncture site when viewed from an angle of 45 degrees away from a normal axis to the top plate is less than 3 mm away from an alignment of the location indicium with the puncture site when viewed along the normal axis.

4. The inflatable hemostasis device of claim 1, wherein the location indicium is disposed adjacent a central location of the bladder.

5. The inflatable hemostasis device of claim 1, wherein the location indicium comprises a visibly altered portion of a bladder surface.

6. The inflatable hemostasis device of claim 1, wherein the top plate is rigid.

7. The inflatable hemostasis device of claim 1, wherein the location indicium further comprises contour lines configured to indicate a concentric or non-concentric compression depth profile.

* * * * *